United States Patent [19]

Ho et al.

[11] Patent Number: 4,722,746
[45] Date of Patent: Feb. 2, 1988

[54] VARIABLE VOLUME SAMPLER FOR AEROSOLS AND GASES

[75] Inventors: Jim Y. W. Ho; Jerome P. Bitz, both of Medicine Hat, Canada

[73] Assignee: Her Majesty the Queen in right of Canada, Canada

[21] Appl. No.: 872,012

[22] Filed: Jun. 9, 1986

[30] Foreign Application Priority Data

Jun. 13, 1985 [CA] Canada .................................. 483941

[51] Int. Cl.$^4$ ............................................. B01D 47/02
[52] U.S. Cl. ............................................. 55/247; 55/86; 55/270; 73/863.21
[58] Field of Search .................... 55/247, 86, 270, 255, 55/256; 73/863.21, 863.02, 863.03

[56] References Cited

U.S. PATENT DOCUMENTS

| | | | |
|---|---|---|---|
| 468,408 | 2/1892 | June | 55/256 |
| 1,739,367 | 12/1929 | Love | 55/314 |
| 3,522,734 | 8/1970 | Curby | 73/863.21 |
| 3,965,747 | 6/1976 | McCorkle | 73/863.02 |
| 4,487,746 | 12/1984 | Tahiliani | 55/255 |

FOREIGN PATENT DOCUMENTS 3008240  9/1981  Fed. Rep. of Germany ........ 55/247

Primary Examiner—Bernard Nozick
Attorney, Agent, or Firm—Stevens, Davis, Miller & Mosher

[57] ABSTRACT

In a method and an apparatus for collecting components of a gaseous medium in a liquid, the gaseous medium is injected into a vessel containing a body of the liquid, below the surface of the liquid and directly into an homogenizer that subjects the bubbles of gaseous medium to a vigorous mechanical homogenizing action.

4 Claims, 3 Drawing Figures

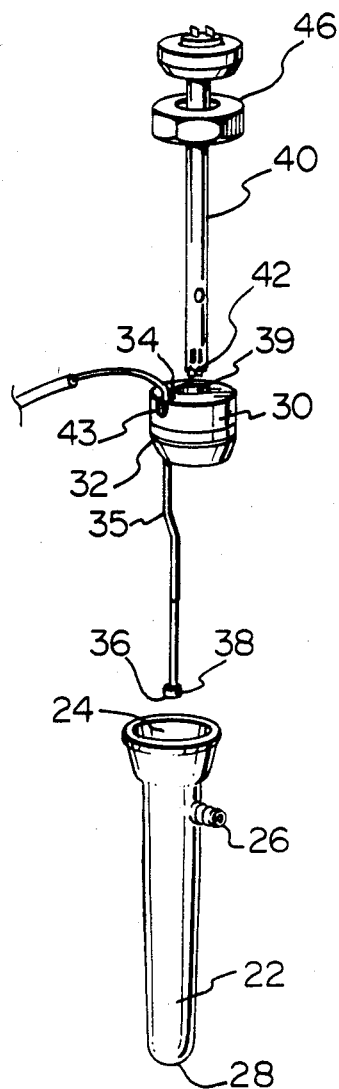
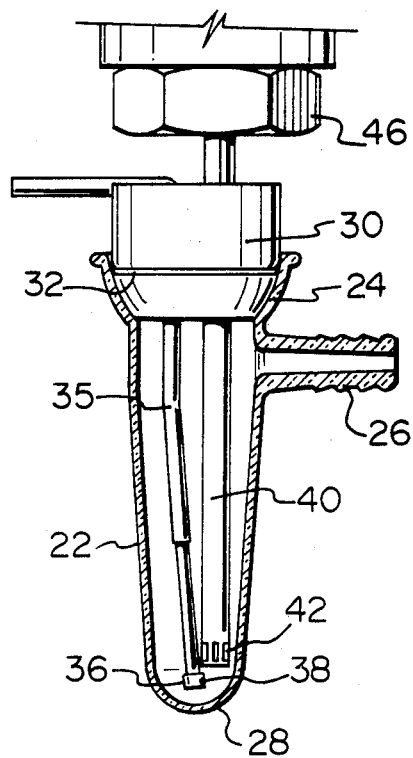
FIG. 2
FIG. 3

VARIABLE VOLUME SAMPLER FOR AEROSOLS AND GASES

FIELD OF THE PRESENT INVENTION

The present invention relates to the collection of samples from gaseous media, and has particular application to the collection of suspended material from aerosols. The invention will be discussed in the following with particular reference to its applicability to aerosols.

BACKGROUND

An aerosol is a suspension of small solid or liquid particles in a gas. Such suspensions may occur naturally or may be man made. The particles in the aerosol may be bacteria, fungi, viruses, toxins, various solid or liquid chemicals and so on. There is a need for the qualitative and quantitative analysis of this type of suspension. In order to analyse an aerosol, at least the component of interest must be collected. This may be done by dissolving or suspending the component in a liquid. According to current practice, this is done with "bubblers" and "impingers".

In a bubbler, the aerosol is broken up into a dispersion of small bubbles passing through a body of liquid. With such a device, the collection efficiency for particles of greater than 1 micrometer in size can be low and non reproducible.

In an impinger, a high speed jet of aerosol is directed against the liquid surface. These devices require high flow rates, thus limiting their utility. It has also been observed that the efficiency of an impinger when dealing with particles composed of two or more organisms is not good.

SUMMARY

The present invention is concerned with a novel method and apparatus for efficiently collecting components of a gaseous medium, for example an aerosol.

According to one aspect of the present invention, there is provided a method of collecting components from a gaseous medium in a liquid comprising injecting a flow of the gaseous medium into a body of the liquid and subjecting the gaseous medium and liquid to a mechanical homogenizing action.

According to another aspect of the present invention there is provided an apparatus for collecting a component of a gaseous medium in a liquid, comprising:
a vessel for containing a body of the liquid;
inlet means for introducing a flow of the gaseous medium into the vessel, below the surface of the body of liquid; and homogenizer means for subjecting the liquid and gaseous medium in the vessel to a mechanical homogenizing action.

With this system, the flow rates of the sample are completely variable. Flow rates can range from a few milliliters per minute to hundreds of liters per minute. At the same time, high collection efficiency may be achieved. This is due to the action of the homogenizer in breaking up "clumps" of particles into individual particles, thus ensuring a more rapid and complete dissolution or suspension of the particles in the liquid.

BRIEF DESCRIPTION OF THE DRAWINGS

In the accompanying drawings, which illustrate an exemplary embodiment of the present invention:

FIG. 2 is an exploded view of a mixer sub-assembly; and

FIG. 3 is an elevation, partially in section, of the mixing chamber in an assembled state.

DETAILED DESCRIPTION

Figure 1:
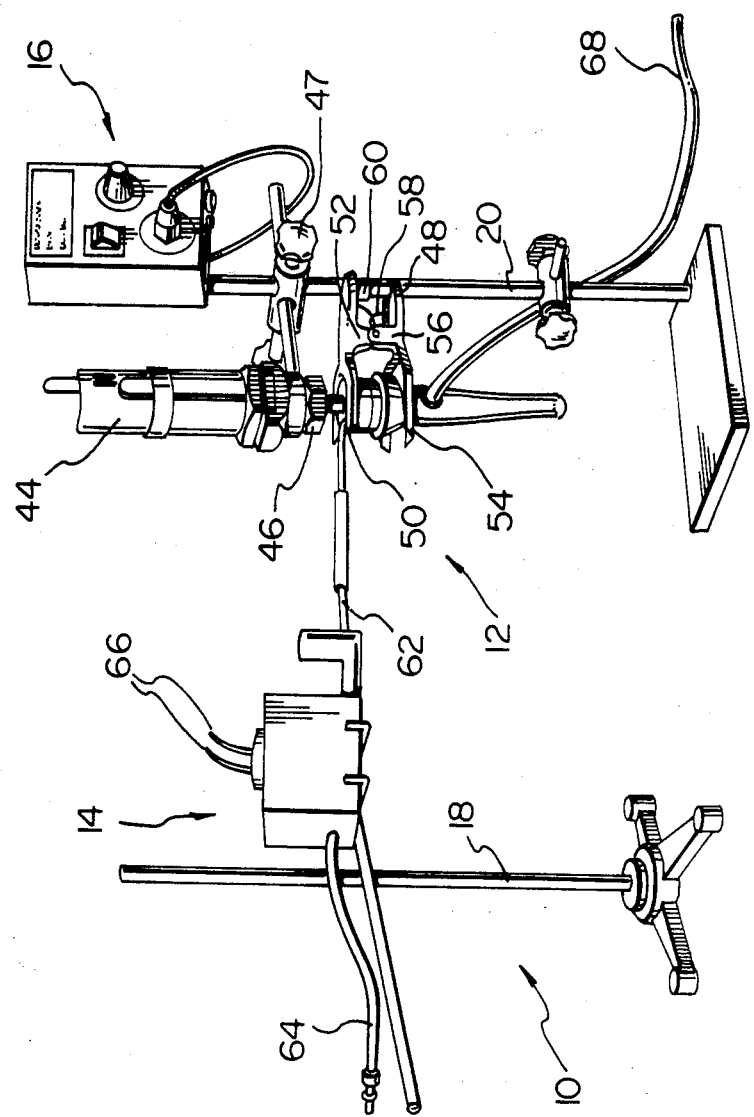
FIG. 1 is a pictorial representation of a laboratory model of the apparatus.

Referring to the drawings, and particularly to FIG. 1, there is illustrated a gaseous medium sampler 10. This comprises a mixer 12, a mass flow controller 14 and a control unit 16 for the flow controller. The flow controller 14 is mounted on a stand 18, while the remaining elements, mixer 12 and control unit 16 are mounted on a stand 20.

Referring now more particularly to FIGS. 2 and 3, the mixer 12 includes a mixing chamber 22 in the form of an elongate glass vessel with an open bell mouth 24. A vacuum outlet 26 is formed in the side wall of the vessel immediately below the mouth 24 and the base 28 of the vessel is rounded, generally hemispherical. The mixer also includes a two-hole stopper 30 that fits into the bell mouth 24 of the mixing chamber 22. The tapered face of the stopper has a peripheral O-ring 32 that provides a seal between the stoppper and the vessel mouth. Stopper hole 34 accommodates an inlet tube 35 while hole 39 accommodates an homogenizing probe 40. The inlet tube 35 extends to near the base 28 of the chamber 22 where it is fitted with a cap 36 with a side orifice 38 to provide a lateral discharge of gas from the tube. The homogenizer probe 40 extends to a position adjacent the base 28 of the chamber 22 so that its impeller 42 is located immediately above the inlet tube cap 36. The orifice in the cap is oriented to discharge into the bottom of the impeller 42. The correct orientation of the inlet tube 35 is maintained by means of a right angle bend at the top end of the tube 35 and a radial slot 43 in the top of the stopper 30, in which the bent-over end of the tube 35 is registered. The homogenizer probe 40 is secured to the end of an homogenizer motor unit 44 with a nut 46. The complete mixer, including the chamber, probe and homogenizer motor is mounted on the stand 20 by means of clamp 47.

A clamp 48 holds the mixing chamber 22 in place on the stopper 30. The clamp has two "Y" shaped arms 50 and 54. The upper arm 50 has a pair of lugs 52 projecting from one side which the lower arm 54 is similarly equipped with lugs 56 pinned to the lugs 52 of the upper arm. A coil spring 58 is located between the arms 50 and 54 to bias the forked ends of the arms towards one another. In use, the fork of the lower arm engages the underside of the bell mouth of the chamber 22, while its upper counterpart engages the top of the stopper 30. The clamp is held in place against accidental release by an adjustable stop 60.

In use, the apparatus is assembled as illustrated in FIG. 1, with the exception of the clamp 48 and the mixing chamber 22. As shown, an inlet tube 62 joins the inlet tube 35 of the mixer to the outlet of the flow controller 14. The flow controller, in turn, has an inlet tube 64. Control cables 66 join the flow controller 14 to the control unit 16. The vacuum outlet 26 of the chamber 22 is connected to a vacuum tube 68. A collecting liquid is then poured into the chamber 22 and the chamber is fitted to the stopper 30. The clamp 48 is installed to hold the chamber 22 on the stopper, and the stop 60 is expanded to prevent inadvertent release of the clamp 48.

After the desired mass flow rate of the aerosol is set using the control unit 16, the flow controller 14, the homogenizer motor unit 44 and the vacuum source are all activated. The vacuum draws aerosol through the flow controller 14 at the set rate, through the inlet tube 35 and out of the orifice 38 into the impeller 42. The impeller produces an exceptionally fine distribution of the aerosol in the liquid. Excess gasses rise to the top of the chamber 22 and are withdrawn to the vacuum source.

It is possible to use a set-up with two of the mixers 12 connected in parallel between the flow controller 14 and the vacuum source by means of two three way solenoid valves, one for the inlet and the other for the vacuum source. With this arrangement, alternate operation of the mixers can give substantially continuous monitoring of an aerosol sample over a selected period of time.

As noted in the foregoing, the apparatus and method disclosed herein are applicable not only to the collection of particulates from aerosols, but may also be used to collect components of other gaseous media, for example a particular gas from a solution of gases.

The flow controller, mixing chamber and homogenizing probe are all interchangeable elements that can be chosen to suit the particular material and flow rate being handled at any given time. In practice the probes come in different sizes that must be matched to a specific vessel and stopper assembly for optimum operation. The optimum mixing speed is determined experimentally in order to obtain the best collection efficiency consistent with an acceptable temperature build-up in the sample. Experience with the system has indicated that cooling has not been necessary, even when collecting bacteria.

While a vacuum is used to draw the gaseous medium into the mixing chamber and some effort has been made to close the chamber, perfect vacuum tightness is not critical with this apparatus.

It will be observed that the design of the mixing chamber and stopper and their assembly through the use of the clamp 48 allows for the very rapid removal and replenishment of the liquid in the chamber.

The embodiments of the invention in which an exclusive property or privilege is claimed are defined as follows:

1. An apparatus for collecting a component of gaseous medium in a liquid, comprising:
    a vessel for containing a body of the liquid;
    homogenizer means for homogenizing the liquid and a gaseous medium in the vessel to produce a suspension or solution of the component in the liquid, the homogenizer means comprising an homogenizer with a elongate probe, the probe having an impeller at a free end thereof that is located adjacent a closed bottom of the vessel; an outlet for withdrawal of gas from the vessel, and
    inlet means for introducing a flow of the gaseous medium into the vessel below the surface of the body of liquid, the inlet means comprising a tube extending into the vessel to a position adjacent the impeller and spaced closer to the bottom of the vessel than the impeller, and an orifice at the end of the tube for directing injected gaseous medium into the impeller.

2. An apparatus according to claim 1, including a mass flow controller connected to the inlet means for controlling the flow rate of the gaseous medium.

3. An apparatus according to claim 2, wherein the vessel is closed except for said outlet.

4. An apparatus according to claim 1 including a stopper closing the vessel, the stopper having openings through which the homogenizer probe and the inlet tube pass.

* * * * *